United States Patent [19]

Gall et al.

[11] 3,957,761

[45] May 18, 1976

[54] PROCESS FOR THE PRODUCTION OF 1-AMINOMETHYL-6-PHENYL-4H-S-TRIAZOLO-[4,3-A][1,4]BENZODIAZEPINES AND INTERMEDIATES

[75] Inventors: Martin Gall, Kalamazoo; Jackson B. Hester, Jr., Galesburg, both of Mich.

[73] Assignee: The Upjohn Company, Kalamazoo, Mich.

[22] Filed: June 19, 1974

[21] Appl. No.: 480,979

Related U.S. Application Data

[63] Continuation-in-part of Ser. No. 332,293, Feb. 14, 1973, Pat. No. 3,842,090.

[52] U.S. Cl.............. 260/240 G; 260/247.2 A; 260/247.5 EP; 260/256.4 Q; 260/268 TR; 260/268 BC; 260/293.59; 260/293.61; 260/308 R
[51] Int. Cl.²............. C07D 209/48; C07D 401/14; C07D 403/06; C07D 487/04
[58] Field of Search...... 260/308 R, 247.1, 247.2 A, 260/247.5 E, 247.5 EP, 268 TR, 293.59, 240 G

[56] References Cited
UNITED STATES PATENTS 3,842,090  10/1974  Gall et al. .................. 260/308 R

*Primary Examiner*—Alton D. Rollins
*Attorney, Agent, or Firm*—Hans L. Berneis

[57] ABSTRACT

A multistep process for the production of a compound of the formula V:

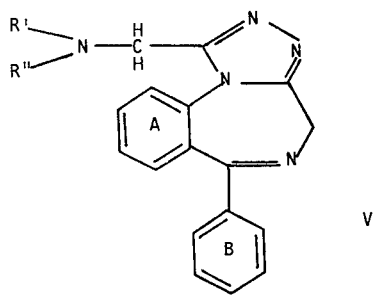

wherein R' and R'' are alkyl of 1 to 3 carbon atoms, inclusive or together

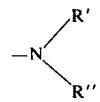

is pyrrolidino, piperidino, 4-methylpiperazino or morpholino; and wherein the rings A and B are unsubstituted, or substituted by one or more substituents selected from the group consisting of fluoro, chloro, bromo, nitro and trifluoromethyl, which comprises treating an equivalent of a compound of formula 1:

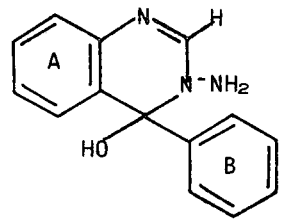

wherein rings A and B are defined as above, with 2 equivalents of an α-phthalimido acetyl halide in an inert organic solvent to obtain a 1,3-dioxo-2-isoindolineacetic acid, [[N-(2-benzoylphenyl)-1,3-dioxo-2-isoindolineacetamido]methylene]hydrazide II which when treated with trifluoroacetic acid gives compound III; treating compound III with a dialkylmethyleneammonium chloride in an inert organic solvent to obtain a 2-[3-(dialkylamino)methyl-5-(phthalimidomethyl)-4H-1,2,4-triazol-4-yl]benzophenone IV and treating IV with hydrazine in an alkanol to obtain a compound V above. Also claimed are the intermediates II and IV.

The 1-aminomethyltriazolobenzodiazepine compounds (V) are used for treatment of anxieties and/or depressions in mammals and birds.

21 Claims, No Drawings

PROCESS FOR THE PRODUCTION OF 1-AMINOMETHYL-6-PHENYL-4H-S-TRIAZOLO-[4,3-a][1,4]BENZODIAZEPINES AND INTERMEDIATES

This application is a continuation in part of application Ser. No. 332,293, filed Feb. 14, 1973, now U.S. Pat. No. 3,842,090.

BACKGROUND OF THE INVENTION

1. Field of the Invention

This invention is directed to organic compounds and is particularly concerned with a novel process for the preparation of 1-aminomethyl-6-phenyl-4H-s-triazolo[4,3-a][1,4]-benzodiazepines and the intermediates thereof.

The novel process or products can be illustratively represented as follows:

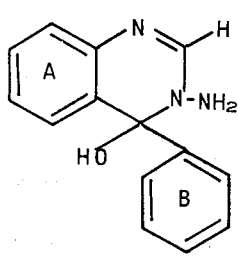

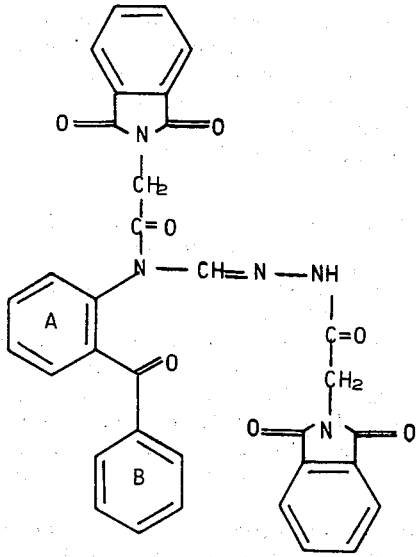

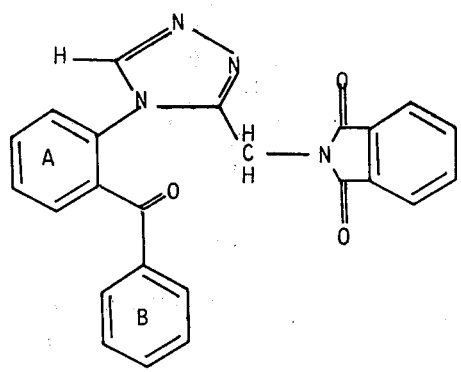

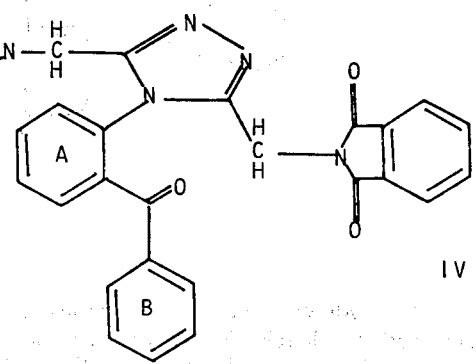

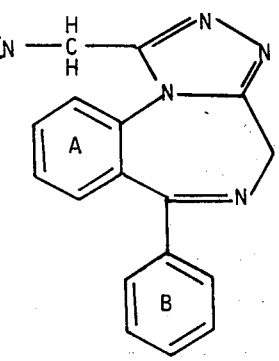

wherein R' and R" are alkyl of 1 to 3 carbon atoms, inclusive or together

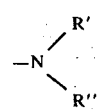

is pyrrolidino, piperidino, 4-methylpiperazino or morpholino.

The invention encompasses besides the process I  II  III  IV  V the novel intermediates of formulae II and IV above.

The more desirable intermediates of the type II have the more specific formula IIA:

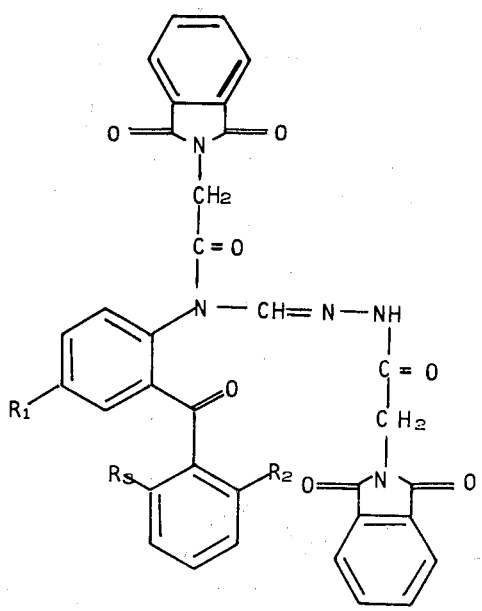

IIA wherein $R_1$ is hydrogen, fluoro, chloro, bromo, nitro, or trifluoromethyl; wherein $R_2$ is hydrogen, fluoro, or chloro; and wherein $R_3$ is hydrogen, or fluoro if $R_2$ is also fluoro.

The most desirable intermediates of type II are of the formula IIB:

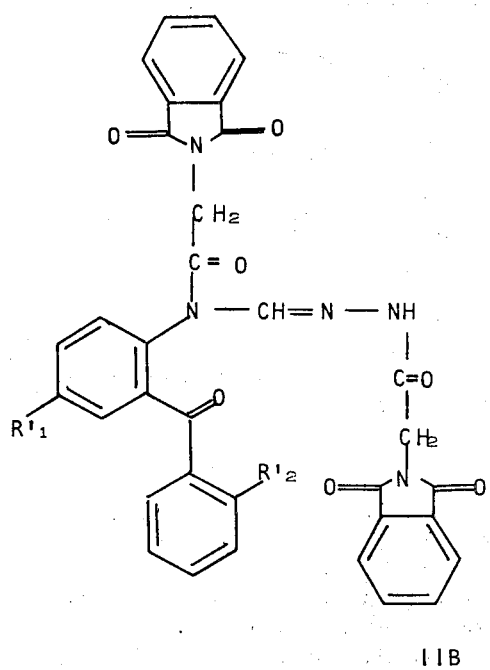

IIB wherein $R'_1$ and $R'_2$ are hydrogen or chloro.

The more desirable products of formula IV have the more specific formula IVA:

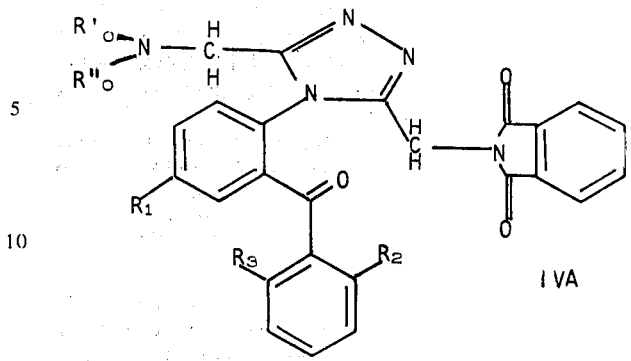

IVA wherein $R'_0$ and $R''_0$ are alkyl of 1 to 3 carbon atoms, inclusive; wherein $R_1$ is hydrogen, fluoro, chloro, bromo, nitro, or trifluoromethyl; wherein $R_2$ is hydrogen, fluoro, chloro; and wherein $R_3$ is hydrogen or fluoro, if $R_2$ is also fluoro.

The most desirable intermediates of type IV have the specific formula IVB:

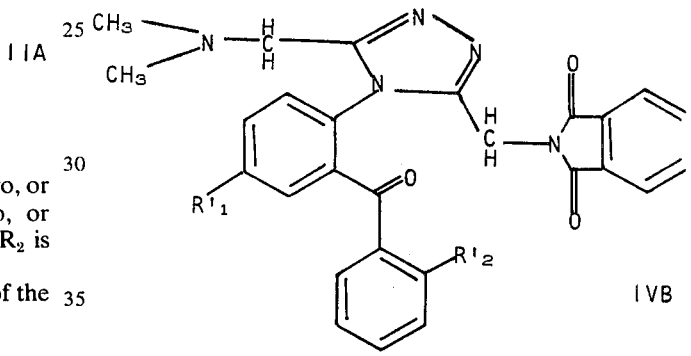

IVB wherein $R'_1$ and $R'_2$ are hydrogen or chlorine.

The process of this invention comprises: treating an equivalent of compound I with two equivalents of α-phthalimidoacetyl chloride or bromide in an inert organic solvent to obtain compound II; treating compound II with trifluoroacetic acid to obtain compound III; treating compound III with a dialkylmethyleneammonium chloride or bromide to obtain compound IV; and treating compound IV with hydrazine in ethanol to obtain compound V above.

DESCRIPTION OF THE PREFERRED EMBODIMENT

Lower alkyl groups of 1 to 3 carbon atoms inclusive, are exemplified by methyl, ethyl, propyl and isopropyl.

The final products of formula V are known compounds, active as tranquilizing, antianxiety and antidepressant agents which are useful in the treatment of mammals and birds. Single unit dosage forms between 0.02 and 1 mg./kg are used as described in detail in the parent application Ser. No. 332,293, filed Feb. 14, 1973.

The object of this invention is the new process for the production of compounds of formula V and the new intermediates II and IV in this process.

Some of the starting compounds of formula I are described in the art by Derieg et al., J. Org. Chem. 36,783 (1971). Other substituted compounds of formula I are made by the same process using the well-known and available substituted 2-aminobenzophenones VI:

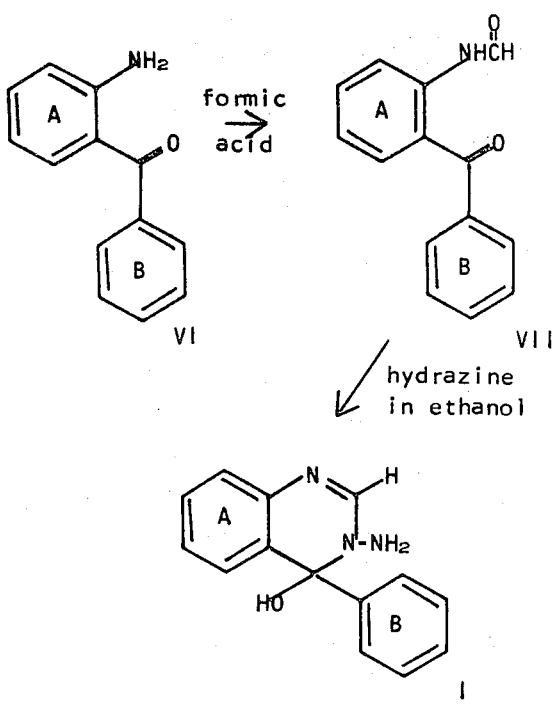

in which the rings A and B are unsubstituted or substituted as described above.

In carrying out the process of the present invention a selected 3-amino-3,4-dihydro-4-hydroxy-4-phenylquinazoline I is suspended in an inert organic solvent e.g., ethylene dichloride, chloroform, carbon tetrachloride, tetrahydrofuran, dioxane or the like, in the presence of an organic base. To this suspension is added α-phthalimidoacetyl chloride or bromide [C. Ainsworth et al., J. Am. Chem. Soc. 76, 5651 (1954)]. In the preferred embodiment of this invention, the reaction is carried out in a nitrogen atmosphere with 2 to 2.5 mol equivalents pyridine as base, and a similar amount of the α-phthalimidoacetyl halide reagent in an inert organic solvent is added dropwise during ½ to 3 hours. The preferred temperature during the reaction is from −5° to 15°C. After all of the reagent has been added, the mixture is allowed to stand from ½ to 2 hours at −5 to 15°C., and finally from 1 to 24 hours at room temperature (22° to 28°). At the termination of the reaction, the product II is recovered by conventional means, i.e. adding water and extracting with an organic water-immiscible solvent e.g., chloroform, methylene chloride. The product is purified by conventional means, generally by crystallization.

Compound II is converted to compound III by reacting a solution of compound II in an inert organic solvent with a halogenated acetic acid, e.g., chloroacetic, dichloroacetic, monofluoroacetic, difluoroacetic or trifluoroacetic acid, with trifluoroacetic acid preferred. Solvents such as benzene, toluene, xylene, chlorobenzene are employed. In the preferred embodiment of this invention the solution of compound II is reacted with the trifluoroacetic acid at temperatures between 80° to 125°C. for ½ to 4 hours. Thereafter the product III is recovered and purified by conventional procedures: concentrating the reaction mixture, adding water, neutralizing the acid, extracting with a water-immiscible organic solvent, chromatography and/or crystallization.

Compound III is converted to compound IV by reacting III with a substituted methyleneammonium halide prepared as shown by H. Bohme et al., Chem. Ber. 93,1305 (1960) or J. Schreiber et al., Angew. Chem., int. ed. 10, 330 (1971). The dialkylmethyleneammonium halide can be prepared also in situ rather than being preformed and added subsequently to the reaction. In the preferred embodiment of this reaction a selected N,N,N,',N'-tetraalkyldiaminomethane in a solvent such as dimethylformamide, diethylformamide, dimethyl- or diethylacetamide or the like, is treated at −5° to 15°C., in a nitrogen atmosphere, with an acylhalide usually acetyl chloride. The mixture is allowed to warm to room temperature (cc. 25°C.) and to stand for ½ to 4 hours at room temperature. To this mixture is added the compound III and the reaction mixture is then allowed to react for 10 to 48 hours at temperatures between 25° to 100°C. Thereafter the reaction mixture is poured into water, neutralized and the precipitated product IV recovered. Product IV is purified by conventional procedures such as recrystallization or chromatography.

Compound IV is converted to compound V by treatment of IV with hydrazine, usually as the hydrate, in a lower alkanol of 1 to 4 carbon atoms between 25°–100°C. Instead of hydrazine, methylamine, ethylamine, propylamine or butylamine and solvents such as tetrahydrofuran, methylene chloride can be used. In the preferred method hydrazine hydrate in ethanol at about the reflux temperature is employed for 1 to 4 hours. The product is recovered and purified by conventional procedures: filtration, extraction, chromatography, crystallization and the like.

The following examples are illustrative of the process and products of the present invention, but are not to be construed as limiting.

EXAMPLE 1

1,3-Dioxo-2-isoindolineacetic acid, [[N-(2-benzoyl-4-chlorophenyl)-1,3-dioxo-2-isoindolineacetamido]-methylene]hydrazide A stirred mixture of 3-amino-6-chloro-3,4-dihydro-4-hydroxy-4-phenylquinazoline (2.74 g, 0.01 mole) in dry tetrahydrofuran (150 ml) is cooled in an ice bath, under nitrogen and treated with dry pyridine (1.77 ml, 1.22 mole). This mixture is then treated, dropwise, during 1 hour, with a solution of α-phthalimidoacetyl chloride (4.92 g, 0.22 mole) in tetrahydrofuran (25 ml). The mixture is kept in the ice bath for 1 hour and at ambient temperature (25°) for 4 hours. It is then poured into ice water and extracted with chloroform. The extract is washed with brine, dried over anhydrous sodium sulfate and concentrated. The solid residue is suspended in ethyl acetate, collected by filtration, washed with ethyl acetate and dried to give 5.36 g of 1,3-dioxo-2-isoindolineacetic acid, [[N-(2-benzoyl-4-chlorophenyl)-1,3-dioxo-2-isoindolineacetamido]methylene]-hydrazide of melting point 167°–172.5°C. (dec.). A small second crop, 0.517 g of melting point 164.5° −167°C dec, is obtained by concentrating the ethyl acetate filtrate. The analytical sample is crystallized from methylene chloride-ethyl acetate and has a melting point 196.5°–198.5°C.

Anal. Calcd. for $C_{34}H_{22}ClN_5O_7$: C, 63.02; H, 3.42; Cl, 5.47; N, 10.81. Found: C, 63.10; H, 3.59; Cl, 5.50; N, 10.97.

EXAMPLE 2

1,3-Dioxo-2-isoindolineacetic acid [[N-[2-(o-chlorobenzoyl)-4-chlorophenyl]-1,3-dioxo-2-isoindolineacetamido]methylene]hydrazide In the manner given in Example 1, 3-amino-6-chloro-3,4-dihydro-4-hydroxy-4-(o-chlorophenyl)quinazoline with pyridine is reacted with α-phthalimidoacetyl chloride to give 1,3-dioxo-2-isoindolineacetic acid [[N-[2-(o-chlorobenzoyl)-4-chlorophenyl]-1,3-dioxo-2-isoindolineacetamido]-methylene]hydrazide.

EXAMPLE 3

1,3-Dioxo-2-isoindolineacetic acid, [[N-[2-(o-chlorobenzoyl)-4-nitrophenyl]-1,3-dioxo-2-isoindolineacetamido]methylene]hydrazide In the manner given in Example 1, 3-amino-6-nitro-3,4-dihydro-4-hydroxy-4-(o-chlorophenyl)quinazoline with pyridine is reacted with α-phthalimidoacetyl chloride to give 1,3-dioxo-2-isoindolineacetic acid, [[N-[2-(o-chlorobenzoyl)-4-nitrophenyl]-1,3-dioxo-2-isoindolineacetamido]methylene]hydrazide.

EXAMPLE 4

1,3-Dioxo-2-isoindolineacetic acid, [[N-[2-(2,6-difluorobenzoyl)-4-chlorophenyl]-1,3-dioxo-2-isoindolineacetamido]methylene]hydrazide In the manner given in Example 1, 3-amino-6-chloro-3,4-dihydro-4-hydroxy-4-(2,6-difluorophenyl)quinazoline with pyridine is reacted with α-phthalimidoacetyl chloride to give 1,3-dioxo-2-isoindolineacetic acid, [[N-[2-(2,6-difluorobenzoyl)-4-chlorophenyl]-1,3-dioxo-2-isoindolineacetamido]methylene]hydrazide.

EXAMPLE 5

1,3-Dioxo-2-isoindolineacetic acid, [[N-[2-(o-chlorobenzoyl)-4-fluorophenyl]-1,3-dioxo-2-isoindolineacetamido]methylene]hydrazide In the manner given in Example 1, 3-amino-6-fluoro-3,4-dihydro-4-hydroxy-4-(o-chlorophenyl)quinazoline with pyridine is reacted with α-phthalimidoacetyl chloride to give 1,3-dioxo-2-isoindolineacetic acid, [[N-[2-(o-chlorobenzoyl)-4-fluorophenyl]-1,3-dioxo-2-isoindolineacetamido]methylene]hydrazide.

EXAMPLE 6

1,3-Dioxo-2-isoindolineacetic acid, [[N-[2-(o-chlorobenzoyl)-4-(trifluoromethyl)phenyl]-1,3-dioxo-2-isoindolineacetamido]methylene]hydrazide In the manner given in Example 1, 3-amino-6-trifluoromethyl-3,4-dihydro-4-hydroxy-4-(o-chlorophenyl)quinazoline with pyridine is reacted with α-phthalimidoacetyl chloride to give 1,3-dioxo-2-isoindolineacetic acid, [[N-[2-(o-chlorobenzoyl)-4-(trifluoromethyl)phenyl]-1,3-dioxo-2-isoindolineacetamido]methylene]hydrazide.

In the manner given in the preceding examples other compounds of formula II structure can be synthesized. Representative compounds thus obtained include:

1,3-dioxo-2-isoindolineacetic acid, [[N-[2-(o-fluorobenzoyl)-4-chlorophenyl]-1,3-dioxo-2-isoindolineacetamido]methylene]hydrazide;

1,3-dioxo-2-isoindolineacetic acid, [[N-[2-benzoyl-4-nitrophenyl]-1,3-dioxo-2-isoindolineacetamido]methylene]hydrazide;

1,3-dioxo-2-isoindolineacetic acid, [[N-[2-benzoyl-4-(trifluoromethyl)phenyl]-1,3-dioxo-2-isoindolineacetamido]methylene]hydrazide;

1,3-dioxo-2-isoindolineacetic acid, [[N-[2-benzoyl-4-fluorophenyl]-1,3-dioxo-2-isoindolineacetamido]methylene]hydrazide;

1,3-dioxo-2-isoindolineacetic acid, [[N-[2-benzoyl-3-nitrophenyl[-1,3-dioxo-2-isoindolineacetamido]methylene]hydrazide;

1,3-dioxo-2-isoindolineacetic acid, [[N-[2-(m-bromobenzoyl)-4-chlorophenyl]-1,3-dioxo-2-isoindolineacetamido]methylene]hydrazide;

1,3-dioxo-2-isoindolineacetic acid, [[N-[2-(o-bromobenzoyl)-5-nitrophenyl]-1,3-dioxo-2-isoindolineacetamido]methylene]hydrazide;

1,3-dioxo-2-isoindolineacetic acid, [[N-[2-(p-bromobenzoyl)-6-fluorophenyl]-1,3-dioxo-2-isoindolineacetamido]methylene]hydrazide;

1,3-dioxo-2-isoindolineacetic acid, [[N-[2-( 2,6-difluorobenzoyl)-5-bromophenyl]-1,3-dioxo-2-isoindolineacetamido]methylene]hydrazide;

1,3-dioxo-2-isoindolineacetic acid, [[N-[2-(p-chlorobenzoyl)-3-nitrophenyl]-1,3-dioxo-2-isoindolineacetamido]methylene]hydrazide;

1,3-dioxo-2-isoindolineacetic acid, [[N-[2-(m-fluorobenzoyl)-3-fluorophenyl]-1,3-dioxo-2-isoindolineacetamido]methylene]hydrazide;

1,3-dioxo-2-isoindolineacetic acid, [[N-(2-benzoyl-3-chlorophenyl)-1,3-dioxo-2-isoindolineacetamido]methylene]hydrazide;

1,3-dioxo-2-isoindolineacetic acid, [[N-[2-(o-chlorobenzoyl)-5-(trifluoromethyl)phenyl]-1,3-dioxo-2-isoindolineacetamido]methylene]hydrazide;

1,3-dioxo-2-isoindolineacetic acid, [[N-[2-(o-chlorobenzoyl)-6-chlorophenyl]-1,3-dioxo-2-isoindolineacetamido]methylene]hydrazide;

1,3-dioxo-2-isoindolineacetic acid, [[N-(2-benzoyl-4-bromophenyl)-1,3-dioxo-2-isoindolineacetamido]methylene]hydrazide;

1,3-dioxo-2-isoindolineacetic acid, [[N-(2-benzoylphenyl)-1,3-dioxo-2-isoindolineacetamido]methylene]hydrazide; and the like.

EXAMPLE 7

5-Chloro-2-[3-(phthalimidomethyl)-4H-1,2,4-triazol-4-yl]benzophenone

A stirred mixture of 1,3-dioxo-2-isoindolineacetic acid, [[N-(2-benzoyl-4-chlorophenyl)-1,3-dioxo-2-isoindolineacetamido]methylene]hydrazide (8.0 g, 0.0123 mole) and toluene (200 ml) is treated with trifluoroacetic acid (0.9 ml) and heated to 100°–110°C for 1.5 hours. The mixture is concentrated in vacuo, and the residue is mixed with cold water and chloroform and made alkaline with aqueous sodium hydroxide. This mixture is extracted with chloroform; the extract is washed with brine, dried over anhydrous sodium sulfate and concentrated. The residue is chromatographed on silica gel (400 g) with 1.5% methanol-98.5% chloroform. The product thus obtained is crystallized from methylene chloride-methanol to give: 2.54 g, melting point 228°–228.5°C. and 0.361 g, melting point 229°–230°C. (53% yield) of 5-chloro-2-[3-(phthalimidomethyl)-4H-1,2,4-triazol-4-yl]benzophenone. The analytical sample has a melting point 229.5°–230.5°.

Anal. Calcd. for $C_{24}H_{15}ClN_4O_3$: C, 65.09; H, 3.41; Cl, 8.00; N, 12.65. Found: C, 65.01; H, 3.67; Cl, 8.01; N, 12.84.

EXAMPLE 8

2',5-dichloro-2-[3-(phthalimidomethyl)-4H-1,2,4-triazol-4-yl]benzophenone

In the manner given in Example 7, 1,3-dioxo-2-isoindolineacetic acid, [[N-[2-(o-chlorobenzoyl)-4-chlorophenyl]1,3-dioxo-2-isoindolineacetamido]methylene]-hydrazide is heated to 100°–110°C with trifluoroacetic acid to give 2',5-dichloro-2-[3-(phthalimidomethyl)-4H-1,2,4-triazol-4-yl]benzophenone.

EXAMPLE 9

2'-Chloro-5-nitro-2-[3-(phthalimidomethyl)-4H-1,2,4-triazol-4-yl]benzophenone

In the manner given in Example 7, 1,3-dioxo-2-isoindolineacetic acid, [[N-[2-(o-chlorobenzoyl)-4-nitrophenyl]-1,3-dioxo-2-isoindolineacetamido]methylene]hydrazide is heated to 100°–110°C with trifluoroacetic acid to give 2'-chloro-5-nitro-2-[3-(phthalimidomethyl)-4H-1,2,4-triazol-4-yl]benzophenone.

EXAMPLE 10

2',6'-Difluoro-5-chloro-2-(phathalimidomethyl)-4H-1,2,4-triazol-4-yl]benzophenone In the manner given in Example 7, 1,3-dioxo-2-isoindolineacetic acid, [[N-[2-(2,6-difluorobenzoyl)-4-chlorophenyl]-1,3-dioxo-2-isoindolineacetamido]methylene]hydrazide is heated to 100°–110°C. with trifluoroacetic acid to give 2',6'-difluoro-5-chloro-2-[3-(phthalimidomethyl)-4H-1,2,4-triazol-4-yl]benzophenone.

EXAMPLE 11

2'-Chloro-5-fluoro-2-[3-(phthalimidomethyl)-4H-1,2,4-triazol-4-yl]benzophenone

In the manner given in Example 7, 1,3-dioxo-2-isoindolineacetic acid, [[N-[2-(o-chlorobenzoyl)-4-fluorophenyl]-1,3-dioxo-2-isoindolineacetamido]methylene]hydrazide is heated to 100°–110°C with trifluoroacetic acid to give 2'-chloro-5-fluoro-2-[3-(phthalimidomethyl)-4H-1,2,4-triazol-4-yl]benzophenone.

EXAMPLE 12

2'-Chloro-5-trifluoromethyl-2-[3-(phthalimidomethyl)-4H-1,2,4-triazol-4-yl]benzophenone In the manner given in Example 7, 1,3-dioxo-2-isoindolineacetic acid, [[N-[2-(o-chlorobenzoyl)-4-(trifluoromethyl)phenyl]-1,3-dioxo-2-isoindolineacetamido]methylene] hydrazide is heated to 100°–110°C. with trifluoroacetic acid to give 2'-chloro-5-trifluoromethyl-2-[3-(phthalimidomethyl)-4H-1,2,4-triazol-4-yl]benzophenone.

In the manner given in Example 7 other 2-[3-(phthalimidomethyl)-4H-1,2,4-triazol-4-yl]benzophenones of formula III can be synthesized. Representative compounds thus obtained include:

5-chloro-2'-fluoro-2-[3-(phthalimidomethyl)-4H-1,2,4-triazol-4-yl]benzophenone;
5-nitro-2-[3-(phthalimidomethyl)-4H-1,2,4-triazol-4-yl]benzophenone;
5-trifluoromethyl-2-[3-(phthalimidomethyl)-4H-1,2,4-triazol-4-yl]benzophenone;
5-fluoro-2-[3-(phthalimidomethyl)-4H-1,2,4-triazol-4-yl]benzophenone;
6-nitro-2-[3-(phthalimidomethyl)-4H-1,2,4-triazol-4-yl]benzophenone;
3'-bromo-5-chloro-2-[3-(phthalimidomethyl)-4H-1,2,4-triazol-4-yl]benzophenone;
2'-bromo-4-nitro-2-[3-(phthalimidomethyl)-4H-1,2,4-triazol-4-yl]benzophenone;
4'-bromo-3-fluoro-2-[3-(phthalimidomethyl)-4H-1,2,4-triazol-4-yl]benzophenone;
2',6'-difluoro-4-bromo-2-[3-(phthalimidomethyl)-4H-1,2,4-triazol-4-yl]benzophenone;
4'-chloro-6-nitro-2-[3-(phthalimidomethyl)-4H-1,2,4-triazol-4-yl]benzophenone;
3'-fluoro-6-fluoro-2-[3-(phthalimidomethyl)-4H-1,2,4-triazol-4-yl]benzophenone;
6-chloro-2-[3-(phthalimidomethyl)-4H-1,2,4-triazol-4 -yl]benzophenone;
2'-chloro-4-trifluoromethyl-2-[3-(phthalimidomethyl)-4H-1,2,4-triazol-4-yl]benzophenone;
2'-chloro-3-chloro-2-[3-(phthalimidomethyl)-4H-1,2,4-triazol-4-yl]benzophenone;
5-bromo-2-[3-(phthalimidomethyl)-4H-1,2,4-triazol-4-yl]-benzophenone;
2-[3-(phthalimidomethyl)-4H-1,2,4-triazol-4-yl]benzophenone;
and the like.

EXAMPLE 13

5-Chloro-2-[3-[(dimethylamino)methyl]-5-(phthalimidomethyl)-4H-1,2,4-triazol-4-yl]benzophenone A stirred solution of N,N,N',N'-tetramethyldiaminomethane (1.531 g, 0.015 mole) in dry dimethylformamide (45 ml) is cooled in an ice bath, under nitrogen, and treated dropwise with freshly distilled acetyl chloride (1.06 ml, 0.015 mole). The resulting suspension is allowed to warm to 25°C. and stand for about 2 hours. 5-Chloro-2-[3-(phthalimidomethyl)-4H-1,2,4-triazol-4-yl]benzophenone (4.429 g, 0.01 mole) is added and the resulting mixture is kept at 50°–54°C for 25 hours. It is then cooled and poured into cold water. The resulting solution is neutralized with sodium bicarbonate. The product which precipitates is collected by filtration, washed with water and dissolved in methylene chloride. The methylene chloride solution is washed with water and brine, dried over anhydrous sodium sulfate and concentrated. The residue is crystallized from methylene chloride-methanol, decolorized with activated carbn (Darco) to give: 4.02 g, melting pont 206°–207.5°C and 0.224 g. melting pont 206°–208.5°C of 5-chloro-2 -[3-[(dimethylamino)methyl]-5-(phthalimidomethyl)-4H-1,2,4-triazol-4-yl]benzophenone. The analytical sample has a melting point 206.5°–208.5°C.

Anal. Calcd, for $C_{27}H_{22}ClN_5O_3$: C, 64.87; H, 4.44; Cl, 7.09; N, 14.01. Found: C, 64.51; H, 4.59; Cl, 7.17; N, 13.90.

EXAMPLE 14

2',5-dichloro-2-[3-[(dimethylamino)methyl]-5-(phthalimidomethyl)-4H-1,2,4-triazol-4-yl]benzophenone In the manner given in Example 13, N,N,N',N'-tetramethyldiaminomethane and acetyl chloride were reacted together in dimethylformamide to give a suspension of dimethylmethyleneammonium chloride.

This suspension is reacted with 2',5-dichloro-2-]3-(phthalimidomethyl)-4H-1,2,4-triazol-4-yl]benzophenone to give 2',5-dichloro-2-[3-[(dimethylamino)methyl]-5-(phthalimidomethyl)-4H-1,2,4-triazol-4-yl]benzophenone.

EXAMPLE 15

2'-Chloro-5-nitro-2-[3-[(dimethylamino)methyl]-5-(phthalimidomethyl)-4H-1,2,4-triazol-4-yl]benzophenone In the manner given in Example 13, N,N,N',N'-tetramethyldiaminomethane and acetyl chloride were reacted together in dimethylformamide to give a suspension of dimethylmethyleneammonium chloride.

This suspension is reacted with 2'-chloro-5-nitro-2-[3-(phthalimidomethyl)-4H-1,2,4-triazol-4-yl]benzophenone to give 2'-chloro-5-nitro-2-[3-[(dimethylamino)methyl]-5-(phthalimidomethyl)-4H-1,2,4-triazol-4-yl]benzophenone.

EXAMPLE 16

2',6'-Difluoro-5-chloro-2-[3-[(dimethylamino)-methyl]-5-(phthalimidomethyl)-4H-1,2,4-triazol-4-yl]benzophenone In the manner given in Example 13, N,N,N',N'-tetramethyldiaminomethane and acetyl chloride were reacted together in dimethylformamide to give a suspension of dimethylmethyleneammonium chloride.

This suspension is reacted with 2',6'-difluoro-5-chloro-2-[3-(phthalimidomethyl)-4H-1,2,4-triazol-4-yl]-benzophenone to give 2',6'-difluoro-5-chloro-2-[3-[(dimethylamino)methyl]-5-(phthalimidomethyl)-4H-1,2,4-triazol-4-yl]benzophenone.

EXAMPLE 17

2'-Chloro-5-fluoro-2-[3-[(dimethylamino)methyl]-5-(phthalimidomethyl)-4H-1,2,4-triazol-4-yl]-benzophenone In the manner given in Example 13, N,N,N',N'-tetramethyldiaminomethane and acetyl chloride were reacted together in dimethylformamide to give a suspension of dimethylmethyleneammonium chloride.

This suspension is reacted with 2'-chloro-5-fluoro-2-[3-(phthalimidomethyl)-4H-1,2,4-triazol-4-yl]benzophenone to give 2'-chloro-5-fluoro-2-[3-[(dimethylamino)methyl]-5-(phthalimidomethyl)-4H-1,2,4-triazol-4-yl]benzophenone.

EXAMPLE 18

2'-Chloro-5-trifluoromethyl-2-[3-[(dimethylamino)-methyl]-5-(phthalimidomethyl)-4H-1,2,4-triazol-4-yl]benzophenone In the manner given in Example 13, N,N,N',N'-tetramethyldiaminomethane and acetyl chloride were reacted together in dimethylformamide to give a suspension of dimethylmethyleneammonium chloride.

This suspension is reacted with 2'-chloro-5-trifluoromethyl-2-[3-(phthalimidomethyl)-4H-1,2,4-triazol-4-yl]benzophenone to give 2'-chloro-5-trifluoromethyl-2-[3-[(dimethyl-amino)methyl]-5-(phthalimidomethyl)-4H-1,2,4-triazol-4-yl]-benzophenone In the manner given in Example 13, other 2-[3-[(dimethylamino)methyl]-5-(phthalimidomethyl)-4H-1,2,4-triazol-4-yl]benzophenones of formula IV can be synthesized.

Representative compounds, thus obtained, include:
5-chloro-2'-fluoro-2-[3-[(dimethylamino)methyl]-5-(phthalimidomethyl)-4H-1,2,4-triazol-4-yl]benzophenone;

5-nitro-2-[3-[(dimethylamino)methyl]-5-(phthalimidometyl)-4H-1,2,4-triazol-4-yl]benzophenone;

5-trifluoromethyl-2-[3-[(dimethylamino)methyl]-5-(phthalimidomethyl)-4H-1,2,4-triazol-4-yl]benzophenone;

5-fluoro-2-[3-[(dimethylamino)methyl]-5-(phthalimidomethyl)-4H-1,2,4-triazol-4-yl]benzophenone;

6-nitro-2-[3-[(dimethylamino)methyl]-5-(phthalimidomethyl)-4H-1,2,4-triazol-4-yl]benzophenone;

3'-bromo-5-chloro-2-[3-[(dimethylamino)methyl]-5-(phthalimidomethyl)-4H-1,2,4-triazol-4-yl]benzophenone;

2'-bromo-4-nitro-2-[3-[(dimethylamino)methyl]-5-(phthalimidomethyl)-4H-1,2,4-triazol-4-yl]benzophenone;

4'-bromo-3-fluoro-2-[3-[(dimethylamino)methyl]-5-(phthalimidomethyl)-4H-1,2,4-triazol-4-yl]benzophenone;

2',6'-difluoro-4-bromo-2-[3-[(dimethylamino)methyl]-5-(phthalimidomethyl)-4H-1,2,4-triazol-4-yl]benzophenone;

4'-chloro-6-nitro-2-[3-[(dimethylamino)methyl]-5-(phthalimidomethyl)-4H-1,2,4-triazol-4-yl]benzophenone;

3'-fluoro-6-fluoro-2-[3-[(dimethylamino)methyl]-5-(phthalimiodomethyl)-4H-1,2,4-triazol-4-yl]benzophenone;

6-chloro-2-[3-[(dimethylamino)methyl]-5-(phthalimidomethyl)-4H-1,2,4-triazol-4-yl]benzophenone;

2'-chloro-4-trifluoromethyl-2-[3-[(dimethylamino)-methyl]-5 -(phthalimidomethyl)-4H-1,2,4-triazol-4-yl]benzophenone; 2'-chloro-3-chloro-2-[3-[(dimethylamino)methyl]-5-(phthalimidomethyl)-4H-1,2,4-triazol-4-yl]benzophenone;

5-bromo-2-[3-[(dimethylamino)methyl]-5-(phthalimidomethyl)-4H-1,2,4-triazol-4-yl]benzophenone;

2-[3-[(dimethylamino)methyl]-5-(phthalimidomethyl)-4H-1,2,4-triazol-4-yl]benzophenone;
and the like.

EXAMPLE 19

5-Chloro-2-[3-[(diethylamino)methyl]-5-(phthalimidomethyl)-4H-1,2,4-triazol-4-yl]benzophenone N,N,N',N'-tetraethyldiaminomethane and acetyl chloride in dimethylformamide were reacted together to give a suspension of N,N-diethylmethyleneammonium chloride.

In the manner given in Example 13, 5-chloro-2-[3-(phthalimidomethyl)-4H-1,2,4-triazol-4-yl]benzophenone is reacted with the above suspension, then neutralized with sodium bicarbonate to give 5-chloro-2-[3-[(diethylamino)-methyl]-5-(phthalimidomethyl)-4H-1,2,4-triazol-4-yl]benzophenone.

EXAMPLE 20

2',5-Dichloro-2-[3-[(ethylmethylamino)methyl]-5-(phthalimidomethyl)-4H-1,2,4-triazol-4-yl]benzophenone N,N'-dimethyl-N,N'-diethyldiaminomethane and acetyl chloride in dimethylformamide were reacted together to give a suspension of N-methyl-N-ethylmethyleneammonium chloride.

In the manner given in Example H-2',5-dichloro-2-[3-(phthalimidomethyl)-4H1,2,4-triazol-4-yl]benzophenone is reacted with the above suspension, then neutralized with sodium bicarbonate to give 2',5-dichloro-2-[3-[(ethyl-methylamino)methyl]-5-(phthalimidomethyl)-4H-1,2,4-triazol-4-yl]benzophenone.

EXAMPLE 21

5-Chloro-2-[3-[(dipropylamino)methyl]-5-(phthalimidomethyl)-4H-1,2,4-triazol-4-yl]benzophenone N,N,N',N'-tetrapropyldiaminomethane and acetyl chloride in dimethylformamide were reacted together to give a suspension of N,N-diproylmethyleneammonium chloride.

In the manner given in Example 13, 5-chloro-2-[3-(phthalimidomethyl)-4H-1,2,4-triazol-4-yl]benzophenone is reacted with the above suspension then neutralized with sodium bicarbonate to give 5-chloro-2-[3-[(dipropylamino)-methyl]-5-(phthalimidomethyl)-4H-1,2,4-triazol-4-yl]-benzophenone.

EXAMPLE 22

2',5-Dichloro-2-[3-[(diisopropylamino)methyl]-5-(phthalimidomethyl)-4H-1,2,4-triazol-4-yl]benzophenone N,N,N',N'-Tetraisopropyldiaminomethane and acetyl chloride in dimethylformamide were reacted together to give a suspension of diisopropylmethyleneammonium chloride.

In the manner given in Example 13, 2',5-dichloro-2-[3-(phthalimidomethyl)-4H-1,2,4-triazol-4-yl]benzophenone is reacted with the above suspension then neutralized with sodium bicarbonate to give 2',5-dichloro-2-[3-[(diisopropylamino)methyl]-5-(phthalimidomethyl)-4H-1,2,4-triazol-4-yl]-benzophenone.

EXAMPLE 23

2'-Chloro-5-nitro-2-[3-(pyrrolidinomethyl)-5-(phthalimidomethyl)-4H-1,2,4-triazol-4-yl]benzophenone Dipyrrolidinomethane and acetyl chloride in dimethylformamide were reacted together to give a suspension of 1-methylenepyrrolidinium chloride.

In the manner given in Example 13, 2'-chloro-5-nitro-2-[3-(phthalimidomethyl)-4H-1,2,4-triazol-4-yl]benzophenone is reacted with the above suspension then neutralized with sodium bicarbonate to give 2'-chloro-5-nitro-2[3-(pyrrolidinomethyl)-5-(phthalimidomethyl)-4H-1,2,4-triazol-4-yl]benzophenone.

EXAMPLE 24

2'-Chloro-5-trifluoromethyl-2-[3-(piperidino-methyl)-5-(phthalimidomethyl)-4H-1,2,4-triazol-4-yl]benzophenone Dipiperidinomethane and acetyl chloride in dimethylformamide are reacted together to give a suspension of 1-methylenepiperidinium chloride.

In the manner given in Example 13, 2'-chloro-5-trifluoromethyl-2-[3-(phthalimidomethyl)-4H-1,2,4-triazol-4-yl]benzophenone is reacted with the above suspension then neutralized with sodium bicarbonate to give 2'-chloro-5-trifluoromethyl-2-[3-(piperidinomethyl)-5-(phthalimidomethyl)-4H-1,2,4-triazol-4-yl]benzophenone.

EXAMPLE 25

2',5-dichloro-2-[3-(4-methylpiperazinomethyl)-5(phthalimidomethyl)-4H-1,2,4-triazol-4-yl]benzophenone Bis(4-methylpiperazino)methane and acetyl chloride in dimethylformamide are reacted together to give a suspension of 4-methyl-1-methylenepiperazinium chloride.

In the manner given in Example 13, 2',5-dichloro-2-[3-(phthalimidomethyl)-4H-1,2,4-triazol-4-yl]benzophenone is reacted with the above suspension then neutralized with sodium bicarbonate to give 2',5-dichloro-2-[3-(4methylpiperazinomethyl)-5-(phthalimidomethyl)-4H-1,2,4-triazol-4-yl]benzophenone.

EXAMPLE 26

2'5-Dichloro-2-[3-(morpholinomethyl)-5-(phthalimidomethyl)-4H-1,2,4-triazol-4-yl]benzophenone Dimorpholinomethane and acetyl chloride in dimethylformamide were reacted together to give a suspension of 4-methylenemorpholinium chloride.

In the manner given in Example 13, 2',5-dichloro-2-[3(phthalimidomethyl)-4H-1,2,4-triazol-4-yl]benzophenone is reacted with the above suspension then neutralized with sodium bicarbonate to give 2',5-dichloro-2-[3-(morpholinomethyl)-5-(phthalimidomethyl)-4H-1,2,4-triazol-4yl]-benzophenone.

EXAMPLE 27

8-Chloro-1-[(dimethylamino)methyl]-6-phenyl-4H-s-triazolo[4,3-a][1,4]benzodiazepine A stirred suspension of 5-chloro-2-[3-[(dimethylamino)-methyl]-5-(phthalimidomethyl)-4H-1,2,4-triazol-4-yl]benzophenone (1.0 g, 0.002 mole) in absolute ethanol (10 ml) is treated with hydrazine hydrate (0.145 ml, 0.003 mole) and warmed ina bath at 70°–77°C for 2 hours. As the reaction progressed the starting material dissolves and a second solid precipitates. The mixture is cooled and filtered. The solid is washed with ethanol and methylene chloride and the combined filtrate is concentrated. The residue is mixed with water and extracted with methylene chloride. The extract is washed with brine, dried over anhydrous sodium sulfate and concentrated. The residue is dissolved in ethyl acetate, filtered through a small pad of silica gel and crystallized from ethyl acetate-Skellysolve B hexanes to give in two crops 0.365 g, melting point 171.5°–174° and 0.078 g, melting point 170.5°–174° of 8-chloro-1-[(dimethylmino)methyl]-6-phenyl-4H-s-triazolo[4,3-a][1,4]benzodiazepine..

EXAMPLE 28

8-Chloro-1-[(dimethylamino)methyl]-6-(o-chlorophenyl)-4H-s-triazolo[4,3-a][1,4]benzodiazepine In the manner given in Example 27, 2′,5-dichloro-2-[3-[(dimethylamino)methyl]-5-(phthalimidomethyl)-4H-1,2,4-triazol-4-yl]benzophenone is heated in ethanol with hydrazine hydrate to give 8-chloro-1-](dimethylamino)methyl]-6-(O-chlorophenyl)-4H-s-triazolo[4,3-a][1,4]benzodiazepine.

EXAMPLE 29

8-nitro-1-(dimethylamino)methyl]-6-(o-chlorophenyl)-4H-s-triazolo[4,3-a][1,4]benzodiazepine In the manner [1,4]benzodiazepin. in Example 27, 2′-chloro-5-nitro2-[3-[(dimethylamino)methyl]-5-(phthalimidomethyl)-4H-1,2,4triazol-4-yl]benzophenone is heated in ethanol with hydrazine hydrate to give 8-nitro-1-[(dimethylamino)methyl]-6-(o-chlorophenyl)-4H-s-triazolo[4,3-a]1,4]benzodiazepin.

EXAMPLE 30

8-Trifluoromethyl-1-(dimethylamino)methyl]-6-(o-chlorophenyl)-4H-s-triazolo[4,3-a][1,4]benzodiazepine In the manner given in Example 27, 2′-chloro-5(trifluoromethyl)-2-[3-[(dimethylamino)methyl]-5-(phthalimidomethyl)-4H-1,2,4-triazol-4-yl]benzophenone is heated in ethanol with hydrazine hydrate to give 8-trifluoromethyl-1-[(dimethylamino)methyl]-6-(o-chlorophenyl)-4H-s-triazolo-[4,3-a][1,4]benzodiazepine.

EXAMPLE 31

8-Fluoro-1-[(dimethylamino)methyl]-6-(o-chlorophenyl)-4H-s-triazolo[4,3-a][1,4]benzodiazepine In the manner given in Example 27, 2′-chloro-5-fluoro-2-[3[(dimethylamino)methyl]-5-(phthalimidomethyl)-4H-1,2,4-triazol-4-yl]benzophenone is heated in ethanol with hydrazine hydrate to give 8-fluoro-1[(dimethylamino)methyl]-6-(o-chlorophenyl)-4H-s-triazolo[4,3-a][1,4]benzodiazepine.

EXAMPLE 32

8-Chloro-1[(dimethylamino)methyl]-6-(2,6-difluorophenyl)-4H-s-triazolo[4,3-a][1,4benzodiazepine In the manner given in Example 27, 2′,6′-difluoro-5-chloro-2-[3-[(dimethylamino)methyl]-5-(phthalimidomethyl)-4H-1,2,4-triazol-4-yl]benzophenone is heated in ethanol with hydrazine hydrate to give 8-chloro-1[(dimethylamino)-methyl]-6-(2,6-difluorophenyl)-4H-s-triazolo[4,3-a][1,4]-benzodiazepine.

EXAMPLE 33

. 8-Chloro-1;
1(diethylamino)methyl]-6-phenyl-4H-s-triazolo[4,3-a][1,4]benzodiazepine In the manner given in Example 27, 5chloro-2-[3-[(diethylamino)methyl]-5-(phthalimidomethyl)-4H-1,2,4-triazol-4-yl]benzophenone is heated in ethanol with hydrazine hydrate to give 8-chloro-1-[(diethylamino)methyl]-6-phenyl-4H-s-triazolo[4,3-a][1,4]benzodiazepine.

EXAMPLE 34

8-Chloro-1-[(ethylmethylamino)methyl]-6-(o-chlorophenyl)-4H-s-triazolo[4,3-a][1,4]benzodiazepine In the manner given in Example 27 ,2′,5-dichloro-2-[3-[(ethylmethylamino)methyl]-5-(phthalimidomethyl)-4H-1,2,4-triazolo-4-yl]benzophenone is heated in ethanol with hydrazine hydrate to give 8-chloro-1-[(ethylmethylamino) -6-(o-chlorophenyl)-4H-s-triazolo[4,3-a][1,4]benzodiazepine.

EXAMPLE 35

8-Chloro-1[(dipropylamino)methyl]-6-phenyl-4H-s-triazolo[4,3-a][1,4benzodiazepine In the manner given in Example 27, 5-chloro-2-[3-[(dipropylamino)methyl]-5-(phthalimidomethyl)-4H1,2,4-triazol-4-yl]benzophenone is heated in ethanol with hydrazine hydrate to give 8-chloro-1-(dipropylamino)methyl]-6-phenyl-4H-s-triazolo[4,3-a][1,4]benzodiazepin.

EXAMPLE 36

8-Chloro-1-[(diisopropylamino)
-6-(o-chlorophenyl)4H-s-triazolo[4,3-a][1,4]benzodiazepine In the manner given in Example 27, 2′,5-dichloro-2-[3-[(diisopropylamino)methyl]-5-(phthalimidomethyl)-4H-1,2,4-triazol-4-yl]benzophenone is heated in ethanol with hydrazine hydrate to give 8-chloro-1-[(diisopropylamino)-methyl]-6-(o-chlorophenyl)-4H-s-triazolo[4,3-a][1,4]benzodiazepine.

EXAMPLE 37

8-Nitro-1-(pyrrolidinomethyl)-6-(o-chloropheyl)-4H-s-triazolo[4,3-a][1,4]benzodiazepine In the manner given in Example 27, 2′-chloro-5-nitro2-[3-(pyrrolidinomethyl)-5-(phthalimidomethyl)-4H-1,2,4-triazol-4-yl]benzophenone is heated in ethanol with hydrazine hydrate to give 8-nitro-1-(pyrrolidinomethyl)-6-(o-chlorophenyl)-4H-s-triazolo[4,3-a][1,4]benzodiazepine.

EXAMPLE 38

8-Trifluoromethyl-1-(piperidinomethyl)-6-(o-chlorophenyl)-4H-s-triazolo[4,3-a][1,4]benzodiazepine In the manner given in Example 27, 2′-chloro-5-trifluoromethyl-2-[3-(piperidinomethyl)-5-(phthalimidomethyl)-4H-1,2,4-triazol-4-yl]benzophenone is heated in ethanol with hydrazine hydrate to give 8-trifluoromethyl-1-(piperidinomethyl)-6-(o-chlorophenyl)-4H-s-triazolo[4,3-a][1,4]-benzodiazepine.

EXAMPLE 39

8-Chloro-1-[(4-methylpiperazino)methyl]-6-(o-chlorophenyl)-4H-s-triazolo[4,3-a][1,4]benzodiazepine In the manner given in Example 27, 2′,5-dichloro-2-[3-[(4-methylpiperazino)methyl]-5-(phthalimidomethyl)-4H-1,2,4-triazol-4-yl]benzophenone is heated in ethanol with hydrazine hydrate to give 8-chloro-1-[4-methylpiperazino)methyl]-6-(o-chlorophenyl)-4H-s-triazolo[4,3-a][1,4]-benzodiazepine.

EXAMPLE 40

8-Chloro-1-(morpholinomethyl)-6-(o-chlorophenyl)-4H-s-triazolo[4,3-a][1,4]benzodiazepine In the manner given in Example 27, 2',5-dichloro-2-[3-(morpholinomethyl)-5-(phthalimidomethyl)-4H-1,2,4-triazol-4-yl]benzophenone is heated in ethanol with hydrazine hydrate to give 8-chloro-1-(morpholinomethyl)-6-(o-chlorophenyl)-4H-s-triazolo[4,3-a][1,4]benzodiazepine.

In the manner given in Example 27, other 1-aminomethyl-6-phenyl-4H-s-triazolo[4,3-a][1,4]benzodiazepines (V) can be synthesized from the corresponding 2-[3-(aminomethyl)5-(phthalimidomethyl)-4H-1,2,4-triazol-4-yl]benzophenones.

Representative compounds, thus obtained, include:

8-chloro-1-[(dimethylamino)methyl]-6-(o-fluorophenyl)-4H-s-triazolo[4,3-a][1,4]benzodiazepine;

8-nitro-1-[(dimethylamino)methyl]-6-phenyl-4H-s-triazolo-[4,3-a][1,4]benzodiazepine;

8-trifluoromethyl-1-[(dimethylamino)methyl]-6-phenyl-4H-s-triazolo[4,3-a][1,4]benzodiazepine;

8-fluoro-1-[(dimethylamino)methyl]-6-phenyl-4H-s-triazolo4,3-a][1,4]benzodiazepine;

7-nitro-1-[(dimethylamino)methyl]-6-phenyl-4H-s-triazol[4,3-a][1,4]benzodiazepine;

8-chloro-1-[(dimethylamino)methyl]-6-(m-bromophenyl)-4H-s-triazolo[4,3-a][1,4-benzodiazepine;

9-nitro-1-[(dimethylamino)methyl]-6-(o-bromophenyl)-4H-s-triazolo[4,3-a][1,4]benzodiazepine;

10-fluoro-1-[(dimethylamino)methyl]-6-(p-bromophenyl)-4H-s-triazolo[4,3-a][1,4]benzodiazepine;

9-bromo-1-[(dimethylamino)methyl]-6-(2,6-difluorophenyl)-4H-s-triazolo[4,3-a][1,4]benzodiazepine;

7-nitro-1-[(dimethylamino)methyl]-6-(p-chlorophenyl-4H-s-triazolo[4,3-a][1,4]benzodiazepine;

7-fluoro-1-[(dimethylamino)methyl]-6-(m-fluorophenyl)-4H-s-triazolo[4,3-a][1,4]benzodiazepine;

7-chloro-1-[(dimethylamino)methyl]-6-phenyl-4H-s-triazolo[4,3-a][1,4]benzodiazepine;

9-trifluoromethyl-1-[(dimethylamino)methyl]-6-(o-chlorophenyl)-4H-s-triazolo[4,3-a][1,4]benzodiazepine;

10-chloro-1-[(dimethylamino)methyl]-6-(o-chlorophenyl)-4H-s-triazolo[4,3-a][1,4]benzodiazepine;

8-bromo-1-[(dimethylamino)methyl]-6 -phenyl-4H-s-triazolo-[4,3-a][1,4]benzodiazepine;

1-[(dimethylamino)methyl]-6-phenyl-4H-s-triazolo[4,3-a]-[1,4]benzodiazepine;

8-nitro-1-[(ethylmethylamino)methyl]-6-(o-chlorophenyl)-4H-s-triazolo[4,3-a][1,4]benzodiazepine;

8-fluoro-1-(pyrrolidinomethyl)-6-(o-chlorophenyl)-4H-s-triazolo[4,3-a][1,4]benzodiazepine;

8-trifluoromethyl-1-(morpholinomethyl)-6-(o-chlorophenyl)-4H-s-triazolo[4,3-a][1,4]benzodiazepine;

9-bromo-1-[(4-methylpiperazino)methyl]-6-(o-chlorophenyl)-4H-s-triazolo[4,3-a][1,4]benzodiazepine;

9-nitro-1-[(diisopropylamino)methyl]-6-phenyl-4H-s-triazolo-[4,3-a][1,4]benzodiazepine;

10-fluoro-1-[(dipropylamino)methyl]-6-phenyl-4H-s-triazolo-[4,2-a][1,4]benzodiazepine;

7-chloro-1-[(diethylamino)methyl]-6-(o-fluorophenyl)-4H-s-triazolo[4,3-a][1,4]benzodiazepine; and the like.

We claim:
1. A process for the production of a compound of formula V:

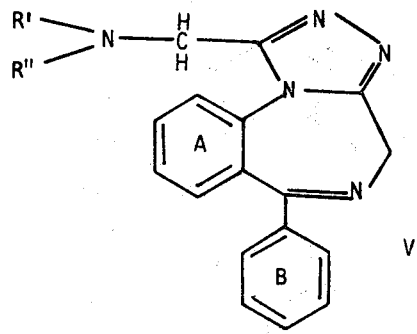

wherein R' and R'' are alkyl of 1 to 3 carbon atoms, inclusive, or

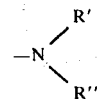

is pyrrolidino, piperidino, 4-methylpiperazino or morpholino, and wherein the rings A and B are unsubstituted, or substituted by one or more substituents selected from the group consisting of fluoro, chloro, bromo, nitro, and trifluoromethyl, which comprises:

1. treating in an inert organic solvent a mole equivalent of a compound of formula I:

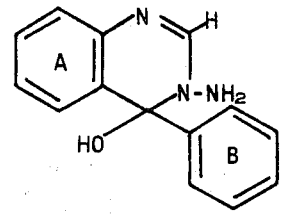

wherein rings A and B are defined as above, with two mole equivalents of α-phthalimidoacetyl chloride or bromide in the presence of an organic base at −5° to +15°C to give the corresponding compound II:

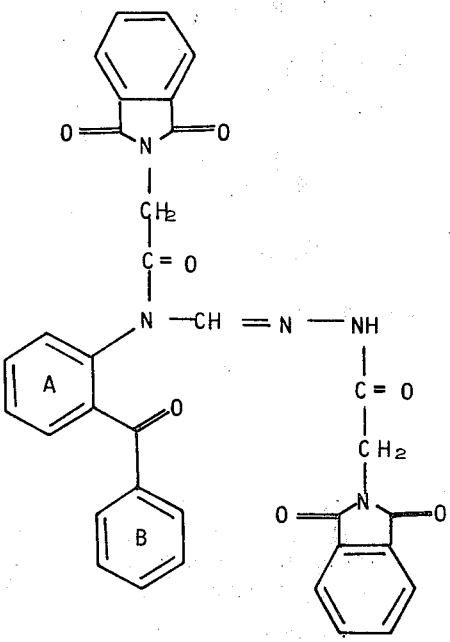

wherein rings A and B are defined as above;
2. treating compound II with a halogenated acetic acid in an inert organic solvent at 80° to 125° C to obtain the corresponding compound III:

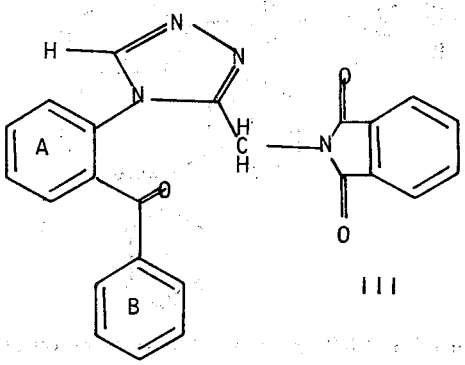

wherein rings A and B have the significance of above;
3. treating compound III with a substituted methyleneammonium halide compound of the formula:

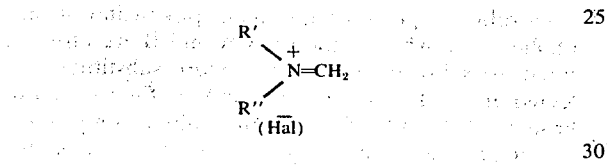

wherein R', R'' or

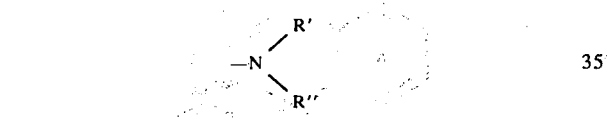

are defined as above and Hal is chlorine or bromine, in a inert organic solvent at 25° to 100° C, to give the corresponding compound IV:

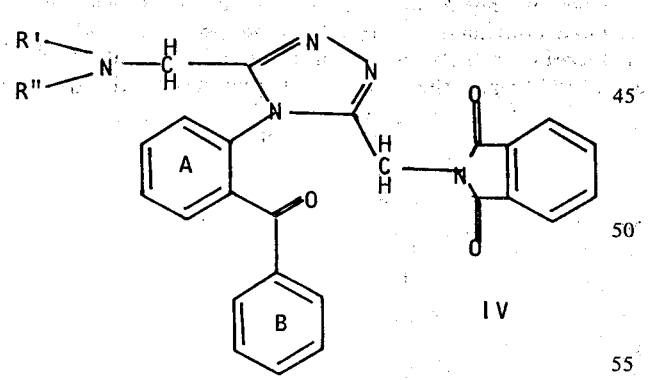

wherein R', R'' or

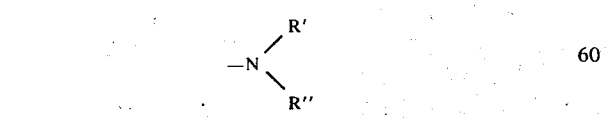

and rings A and B are defined as above;
4. treating compound IV with hydrazine in an alkanol of 1 to 4 carbon atoms, inclusive at 25° to 100° to obtain the corresponding compound V, as defined above.

2. The process according to claim 1 wherein the starting compound 1 is 3-amino-6-chloro-3,4-dihydro-4-hydroxy-4-phenylquinazoline.

3. The process according to claim 1 wherein the starting compound 1 is 3-amino-6-chloro-3,4-dihydro-4-hydroxy-4-(o-chlorophenyl)quinazoline.

4. The process according to claim 1 wherein the starting compound 1 is 3-amino-3,4-dihydro-4-hydroxy-4-phenylquinazoline.

5. The process of claim 1, wherein the substituted methyleneammonium halide is dimethylmethyleneammonium chloride.

6. The process of claim 2, wherein the substituted methyleneammonium halide is dimethylmethyleneammonium chloride.

7. The process of claim 3, wherein the substituted methyleneammonium halide is dimethylmethyleneammonium chloride.

8. The process of claim 4, wherein the substituted methyleneammonium halide is dimethylmethyleneammonium chloride.

9. The process of claim 1, wherein the halogenated acetic acid is trifluoroacetic acid.

10. A compound of the formula II:

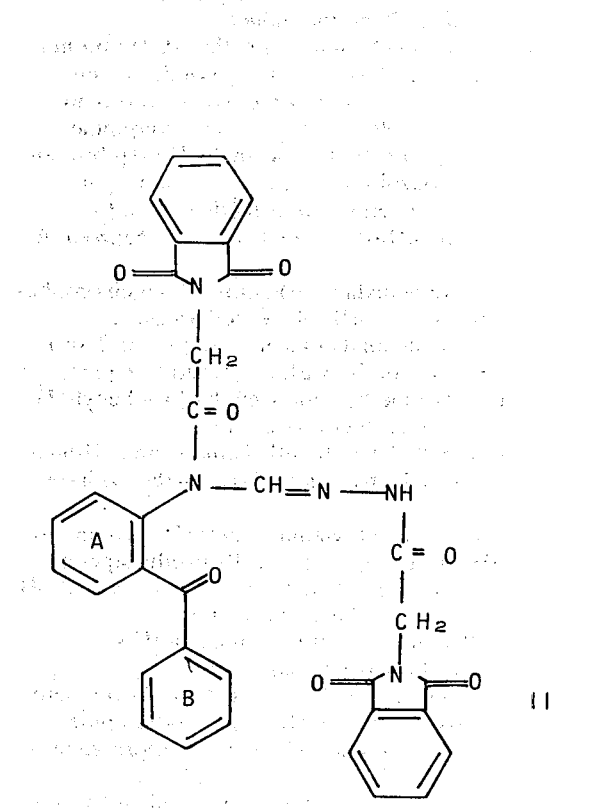

wherein rings A and B are unsubstituted or substituted with one or two substituents selected from the group consisting of fluoro, chloro, bromo, nitro, and trifluoromethyl.

11. A compound according to claim 10 of the formula IIA:

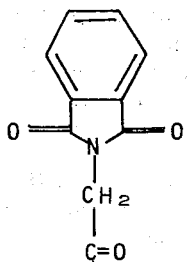

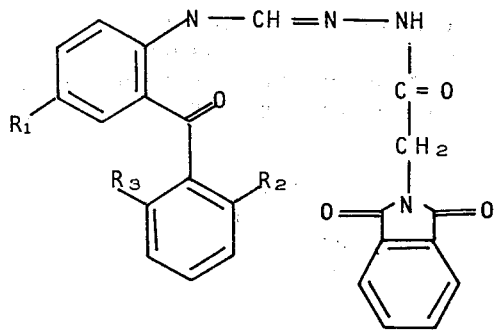

IIA wherein R₁ is hydrogen, fluoro, chloro, bromo, nitro, or trifluoromethyl; wherein R₂ is hydrogen, fluoro or chloro; and wherein R₃ is hydrogen, or fluoro if R₂ is also fluoro.

12. A compound according to claim 10 of the formula IIB:

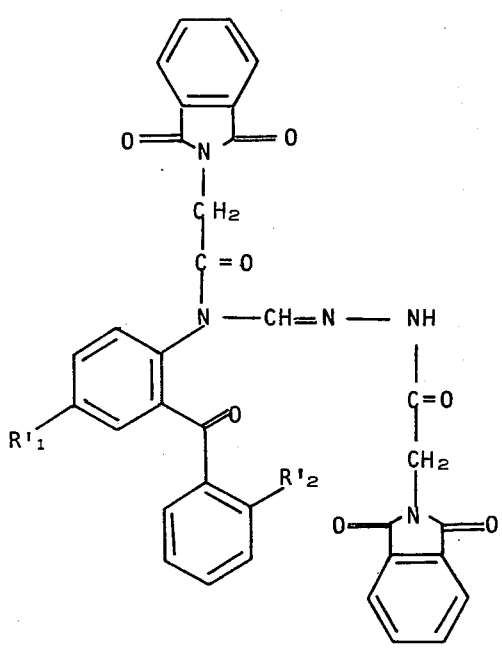

IIB wherein R'₁ and R'₂ are hydrogen or chloro.

13. A compound according to claim 12, wherein R'₁ is chloro, R'₂ is hydrogen and the compound is therefore 1,3-dioxo-2-isoindolineacetic acid, [[N-(2-benzoyl-4-chlorophenyl)-1,3-dioxo-2-isoindolineacetamido]methylene]hydrazide.

14. A compound according to claim 12, wherein R'₁ and R'₂ are chloro and the compound is therefore 1,3-dioxo-2-isoindolineacetic acid, [[N-[2-(o-chlorobenzoyl)-4-chlorophenyl]-1,3-dioxo-2-isoindolineacetamido]methylene]hydrazide.

15. A compound according to claim 12, wherein R'₁ and R'₂ are hydrogen and the compound is therefore 1,3-dioxo-2-isoindolineacetic acid, [[N-(2-benzoylphenyl)-1,3-dioxo-2-isoindolineacetamido]methylene]hydrazide.

16. A compound of the formula IV:

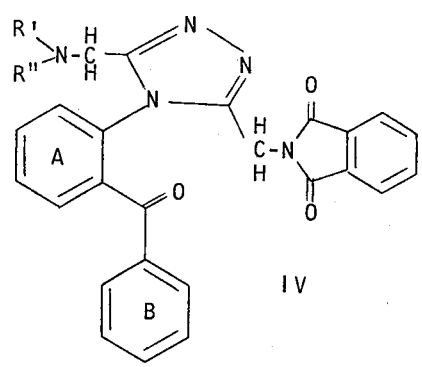

IV wherein R' and R'' are alkyl of 1 to 3 carbon atoms, inclusive, or together

is pyrrolidino, piperidino, morpholino, or N-methylpiperazino and wherein the rings A and B are unsubstituted or substituted with 1 to 2 substituents selected from the group consisting of fluoro, chloro, bromo, nitro, and trifluoromethyl.

17. A compound according to claim 16, of the formula IVA:

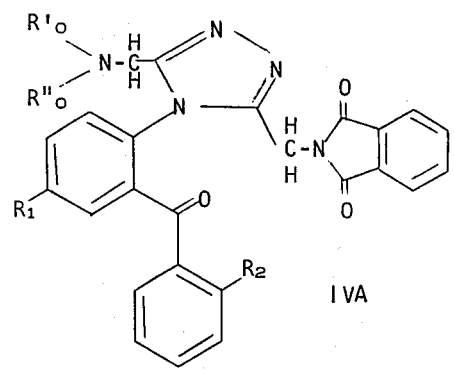

IVA wherein R''₀ and R''₀ are alkyl of 1 to 3 carbon atoms, inclusive; wherein R₁ is hydrogen, fluoro, chloro, bromo, nitro, or trifluoromethyl; wherein $R_2$ is hydrogen, fluoro, or chloro; and wherein $R_3$ is hydrogen or fluoro, if $R_2$ is also fluoro.

18. A compound according to claim 16 of the formula IVB:

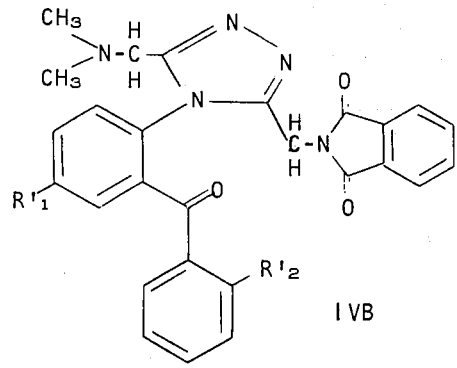

wherein $R'_1$ and $R'_2$ are hydrogen or chlorine.

19. A compound according to claim 18, wherein $R'_1$ is chloro, wherein $R'_2$ is hydrogen and the compound is therefore 5-chloro-2-[3-[(dimethylamino)methyl]-5-(phthalimidomethyl-4H -1,2,4-triazol-4-yl]benzophenone.

20. A compound according to claim 18, wherein $R'_1$ and $R'_2$ are chloro and the compound is therefore 2',5-dichloro-2-[3-[(dimethylamino)methyl]-5-(phthalimidomethyl)-4H-1,2,4-triazol-4-yl]benzophenone.

21. A compound according to claim 18, wherein $R'_1$ and $R'_2$ are hydrogen and the compound is therefore 2-[3-[(dimethylamino)methyl]-5-(phthalimidmethyl)-4H-1,2,4-triazol-4-yl]benzophenone.

* * * * *

UNITED STATES PATENT OFFICE
CERTIFICATE OF CORRECTION

Patent No. 3,957,761                   Dated May 18, 1976

Inventor(s) Martin Gall; Jackson B. Hester, Jr.

It is certified that error appears in the above-identified patent and that said Letters Patent are hereby corrected as shown below:

Column 4, lines 23-38, " 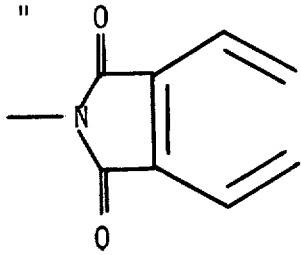 " should read

-- 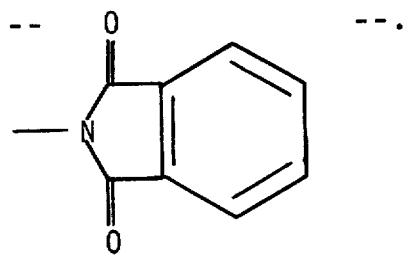 --.

Column 9, line 20, "trifluoracetic" should read -- trifluoroacetic --.
Column 9, line 26, "chloro-2-(phthal" should read -- chloro-2-[3-(phthal --.
Column 10, line 50, "carbn" should read -- carbon --.
Column 10, line 52, "melting pont" should read -- melting point --.
Column 11, line 1, "2-]3-" should read -- 2-[3- --.
Column 11, line 64, "benzophenone" should read -- benzophenone.--
Column 12, line 6, "(phthalimidometyl" should read -- (phthalimidomethyl --.
Column 13, line 11, "Example H" should read -- Example 13 --.

UNITED STATES PATENT OFFICE
CERTIFICATE OF CORRECTION

Patent No. 3,957,761          Dated May 18, 1976

Inventor(s)   Martin Gall; Jackson B. Hester, Jr.

It is certified that error appears in the above-identified patent and that said Letters Patent are hereby corrected as shown below:

Column 13, line 12, "4H1,2,4" should read -- 4H-1,2,4 --.
Column 13, line 26, "N,N-diproyl" should read --N,N-dipropyl--.
Column 14, line 56, "ina" should read -- in a --.
Column 15, line 12, "(O-chloro" should read -- (o-chloro --.
Column 15, line 15, "8-nitro-1-(dimethyl" should read
    -- 8-Nitro-1-[(dimethyl --.
Column 15, line 18, "In the manner [1,4]benzodiazepin. in
    Example 27" should read -- In the manner given in
    Example 27 --.
Column 15, line 19, "nitro2-" should read -- nitro-2- --.
Column 15, line 20, "1,2,4triazol" should read -- 1,2,4-
    triazol --.
Column 15, line 24, "benzodiazepin." should read
    -- benzodiazepine. --.
Column 15, line 26, "1-(dimethyl" should read -- 1-[(dimethyl--.
Column 15, lines 61-62, "8-Chloro:
                    1(diethyl" should read -- 8-Chloro-
    1-[(dimethyl --.
Column 15, line 65, "5chloro" should read -- 5-chloro --.
Column 16, line 12, "amino     -6-" should read
    -- amino)methyl]-6- --.
Column 16, line 16, "[1,4benzo" should read -- [1,4]benzo --.
Column 16, line 20, "4H1,2,4" should read -- 4H-1,2,4 --.
Column 16, line 21, "1-(dipropyl" should read -- 1-[(dipropyl--.
Column 16, line 23, "benzodiazepin." should read -- benzo-
    diazepine. --.
Column 16, lines 26-27, "amino)
                    -6-" should read -- amino)methyl]-6- --.
Column 16, line 27, "4H-" should read -- -4H- --.

UNITED STATES PATENT OFFICE
CERTIFICATE OF CORRECTION

Patent No. 3,957,761         Dated   May 18, 1976

Inventor(s)  Martin Gall; Jackson B. Hester, Jr.

It is certified that error appears in the above-identified patent and that said Letters Patent are hereby corrected as shown below:

Column 16, line 38, "(o-chlorpheyl)" should read
-- (o-chlorophenyl) --.
Column 17, line 25, "triazolo4,3" should read -- triazolo-[4,3 --.
Column 17, line 27, "triazol[4,3-" should read -- triazolo-[4,3- --.
Column 17, line 65, "[4,2-a" should read -- [4,3-a --.
Column 22, Cl. 17, line 67, "wherein R"$_o$ and R"$_o$" should read
-- wherein R'$_o$ and R"$_o$ --.
Column 24, Cl. 21, line 15, "(phthalimidmethyl)" should read
-- (phthalimidomethyl) --.

Signed and Sealed this

Seventeenth Day of July 1979

[SEAL]

Attest:

LUTRELLE F. PARKER

*Attesting Officer*   *Acting Commissioner of Patents and Trademarks*